United States Patent [19]

Michaud et al.

[11] Patent Number: 5,408,855
[45] Date of Patent: Apr. 25, 1995

[54] METHOD FOR CONTINUOUSLY MEASURING MECHANICAL PROPERTIES OF A CONTINUOUSLY PRODUCED SHEET, IN PARTICULAR A SHEET OF STEEL

[75] Inventors: Hervé Michaud, Saint-Etienne; Roland Fortunier, L'Etrat; Marc Friedrich, Metz Vallieres, all of France

[73] Assignee: Sollac, Puteaux, France

[21] Appl. No.: 961,635

[22] Filed: Oct. 16, 1992

[30] Foreign Application Priority Data

Oct. 17, 1991 [FR] France .................. 91 12834

[51] Int. Cl.⁶ .................. B21B 1/24; G01L 5/04
[52] U.S. Cl. .................. 72/31; 72/252.5; 492/38; 73/159
[58] Field of Search .................. 72/17, 31, 37, 199, 72/252.5; 492/9, 28, 30, 38, 57; 33/734; 73/1 B, 159, 862.39, 862.42, 862.46, 862.62

[56] References Cited

U.S. PATENT DOCUMENTS

| | | | |
|---|---|---|---|
| 3,526,113 | 9/1970 | McNaugner | 72/235 |
| 3,750,466 | 8/1973 | Ott et al. | 73/159 |
| 4,356,714 | 11/1982 | Quehen | 73/159 |
| 4,674,310 | 6/1987 | Ginzburg | 72/17 |
| 4,864,851 | 9/1989 | Haughton | 73/159 |
| 4,909,055 | 3/1990 | Blazevic | 72/205 |
| 4,970,895 | 11/1990 | Houghton et al. | 73/159 |
| 5,111,688 | 5/1992 | Houghton et al. | 73/159 |
| 5,123,284 | 6/1992 | Edinburgh et al. | 73/159 |
| 5,138,878 | 8/1992 | Cresson et al. | 73/159 |

FOREIGN PATENT DOCUMENTS

| | | | |
|---|---|---|---|
| 0025646 | 3/1981 | European Pat. Off. | |
| 0253644 | 1/1988 | European Pat. Off. | |
| 257686 | 6/1988 | Germany | |
| 291401 | 6/1991 | Germany | |
| 0178127 | 10/1984 | Japan | 72/37 |
| 0273507 | 11/1988 | Japan | 72/17 |

OTHER PUBLICATIONS

Welding International, vol. 3, No. 11, 1989, A. Noutomi, et al., pp. 947–953, "Residual Stress Measurement On Plasma Sprayed Coatings".

*Primary Examiner*—Lowell A. Larson
*Assistant Examiner*—Thomas C. Schoeffler
*Attorney, Agent, or Firm*—Oblon, Spivak, McClelland, Maier, & Neustadt

[57] ABSTRACT

The method comprises, at a given point of the production line:
   producing on the sheet a known localized deformation which is such that at least in a zone of a surface of the sheet the deformation is partially plastic;
   evaluating in the zone of the plastically deformed surface at least one surface stress.

7 Claims, 2 Drawing Sheets

METHOD FOR CONTINUOUSLY MEASURING MECHANICAL PROPERTIES OF A CONTINUOUSLY PRODUCED SHEET, IN PARTICULAR A SHEET OF STEEL

The invention relates to continuously measuring mechanical properties of a continuously produced sheet or strip, in particular a sheet or strip of steel.

Steel sheets intended, for example, for press forming or drawing are produced on continuous production lines effecting, for example, a cold rolling, an annealing and a skinpass. This complete method imparts to the sheets a geometry characterized by thickness and mechanical properties, in particular a yield point which may vary with the direction in which it is measured. These mechanical properties represent the behavior of the sheets when press formed or drawn and must be monitored.

The technique employed at the present time for monitoring the mechanical properties consists in taking samples and carrying out tension tests. The drawback of this technique is that it is not continuous. It permits effecting localized adjustments in the production line but does not permit regulating the production line.

An object of the present invention is to provide a method for continuously measuring the mechanical properties of a continuously produced sheet, in particular a sheet of steel, which permits regulating the production line.

For this purpose, the invention provides a method for continuously measuring the mechanical properties of a continuously produced sheet, in particular a sheet of steel, comprising, at a given point of the production line:

producing on said sheet a known localized deformation so that, at least in a zone of a surface of the sheet, the deformation is partially plastic;

evaluating in the zone of the surface which undergoes the partially plastic deformation, at least one surface stress in a given direction.

This surface stress gives a good estimation of the yield point of the sheet in said direction.

Preferably, three surface stresses are evaluated:
one in the direction of travel of the sheet;
the second in a direction perpendicular to the direction of travel of the sheet;
the third in a direction oriented at 45° to the direction of travel of the sheet.

In a first embodiment, to produce the deformation of the sheet, the latter is rolled round a roll whose radius is sufficiently small to bring about a plastic deformation by elongation of the outer fibers of the sheet.

In another embodiment, a roll is used whose lateral surface comprises a projecting torus-shaped boss.

The stresses are measured by diffraction of X-rays.

The invention also provides a roll for carrying out the method whose lateral surface has a projecting torus-shaped boss.

The invention will now be described in more detail with reference to the accompanying drawings in which.

When a steel sheet or strip is subjected by a mechanical procedure to a deformation and the deformation and the surface stress are simultaneously measured in the region which is deformed, a stress/strain curve can be plotted which is similar to a tension curve. This curve has first of all a linear part which corresponds to elastic deformation, then, when the deformation is sufficient, a zone in which its stress varies little with increase in deformation. This zone corresponds to plastic deformation and the stress measured represents the yield point of the sheet.

If a deformation is produced which is sufficient to be partially plastic, and if the surface stress is measured, an estimation is then had of the yield point which is close to the measured stress.

The foregoing is the principle underlying the method according to the invention.

In a first embodiment, the sheet is partly rolled or wrapped round a roll of small diameter. For example, for a sheet 0.2 mm thick, the sheet is rolled round a roll 100 mm in diameter.

Figure 1:
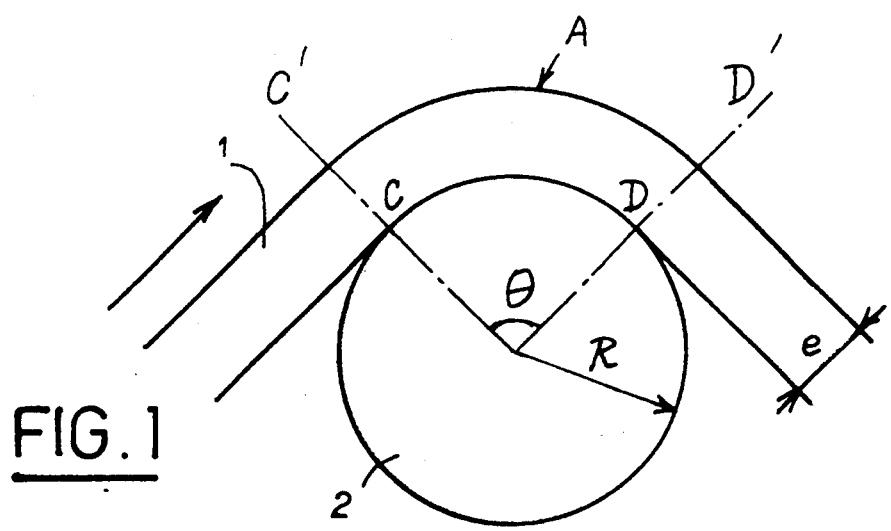
FIG. 1 is a diagrammatic view of a sheet rolled or wrapped round a roll.

As shown in FIG. 1, the sheet 1 having a thickness e is in contact with the roll 2. The neutral fiber having a radius R, defined by the arc CD subtending an angle $\theta$ at its center, does not undergo an elongation in the course of this bending and has a length $\theta.R$. On the outer surface of the sheet which is not in contact with the roll, the sheet is deformed along the arc C'D' of length $$\left(R + \frac{e}{2}\right)\theta.$$

This arc has undergone an elongation equal to $$\frac{\left(R + \frac{e}{2}\right)\theta - R\theta}{R\theta} = \frac{e}{2R}$$

and a stress exists on the surface of the sheet.

If $$\frac{e}{2R}$$

is greater than 0.002 (namely 0.2%) the elongation of the outer fibers of the sheet may be sufficient to ensure that the deformation is plastic and the stress is substantially equal to the yield point in the direction of travel of the sheet.

The stresses are evaluated by diffraction of X-rays in a method which will be described hereinafter.

A cold rolled sheet does not have mechanical properties which are identical in all directions and these properties must be known in at least three directions so as to foresee the behaviour of the sheet when subjected to a press forming or drawing operation. For this purpose, the yield point must be determined in several directions.

To determine the yield point in several directions, a partially plastic deformation in several directions is created, for example by producing a temporary bulge on the sheet, and the surface stresses are measured in several directions. The stresses are for example measured in the direction of travel of the sheet, in a direction perpendicular to the direction of travel of the sheet and in a direction oriented at 45° to the direction of travel of the sheet.

Figure 2:
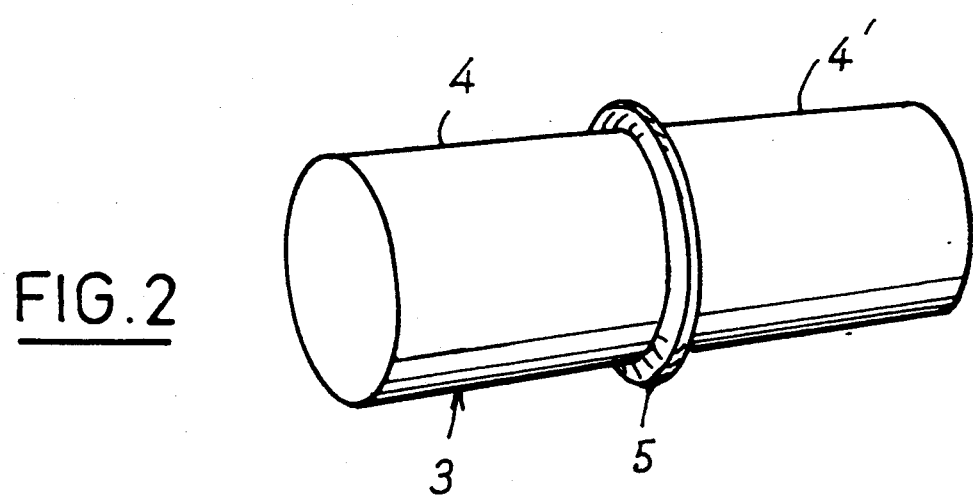
FIG. 2 is a roll comprising a projecting torus-shaped boss according to the invention.

In a second embodiment, the sheet is rolled or wrapped round a roll carrying the general reference character 3 in FIG. 2 and having a cylindrical surface 4, 4' and a projecting torus-shaped boss 5 which imparts to the sheet a temporary deformation in the shape of a bulge.

Figure 3:
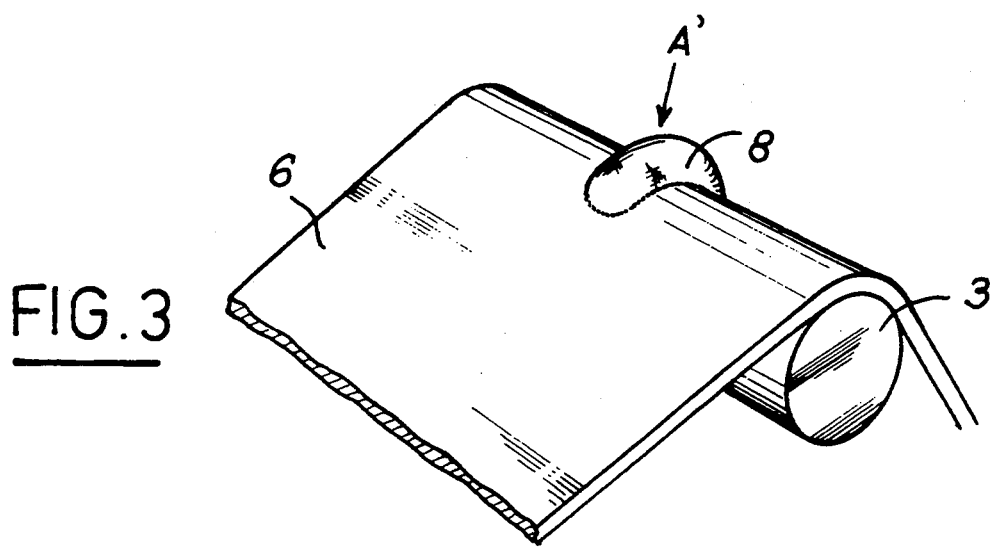
FIG. 3 is a diagrammatic view of deformations produced on a sheet by a roll having a torus-shaped boss.

FIG. 3 shows a sheet 6 travelling in the direction of the arrow and passing round a roll 3 which has a torus-shaped boss. At the place of the torus-shaped boss the sheet forms a bulge 8 which matches the shape of the boss.

This bulge corresponds to a surface deformation of the sheet which occurs not only in the direction of travel of the sheet but also in a perpendicular direction and other directions.

By measuring by diffraction of X-rays the stresses in three directions, namely parallel to, perpendicular to and at 45° to the direction of travel of the sheet, the yield points and the anisotropy of the sheet can be evaluated in these three directions.

These measurements are carried out at place A' of the zone in which the aforementioned plastic deformation occurs.

All these measurements are effected in a continuous manner and can be effected on sheets travelling at at least 600 m/min. This permits employing this method for regulating the production line.

The measurement of the stresses with X-rays is effected by a method whose principles have been widely published and described in particular in the article by G. MEADER: "Present developments of the determination of stresses by diffraction of X-rays" in the review "Matériaux et Techniques" of September/October 1988, pages 5 to 12.

Figure 4:
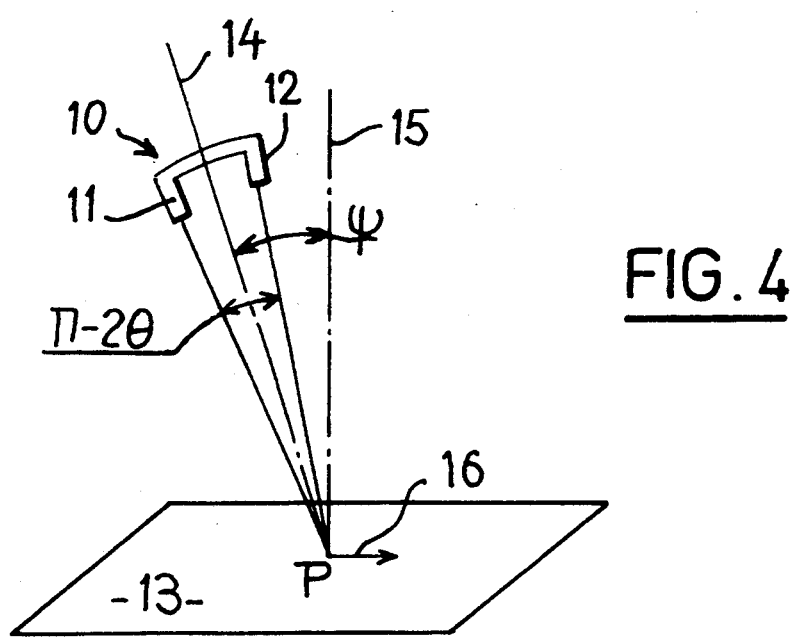
FIG. 4 is a diagrammatic view of a goniometer employed for evaluating the stress by means of X-rays.

Goniometers are employed for carrying out the method. One of these goniometers carries the general reference character 10 in FIG. 4. It comprises an X-ray emitter 11 and a detector 12. The emitter 11 and the detector 12 are aimed at the same point P of the surface 13 to be analyzed. The axes of the emitter 11 and detector 12 make an angle of $\pi - 2\theta$ therebetween. The bisector 14 of the angle made between the axes of the emitter 11 and detector 12 makes an angle $\Psi$ with the perpendicular 15 to the surface 13 to be analyzed. The angle $\Psi$ is determined in the known manner in accordance with the conditions of the analysis to be effected.

The detector permits measuring the Bragg angle $\theta$ which is a characteristic of the diffraction of the X-rays at point P.

When the material analyzed presents stresses, the Bragg angle depends on the angle $\Psi$.

To evaluate a stress, two goniometers are used, one with an angle $\Psi = 0°$ and the other with an angle $\Psi = 60°$ for example. The stress is then proportional to the difference between the Bragg angles measured by each of the detectors. The stress is measured in the direction of arrow 16 parallel to the trace on the surface 13 of the plane defined by the perpendicular 15 to the surface 13 and the bisector 14 of the angle between the axes of the emitter 11 and detector 12.

Figure 5:
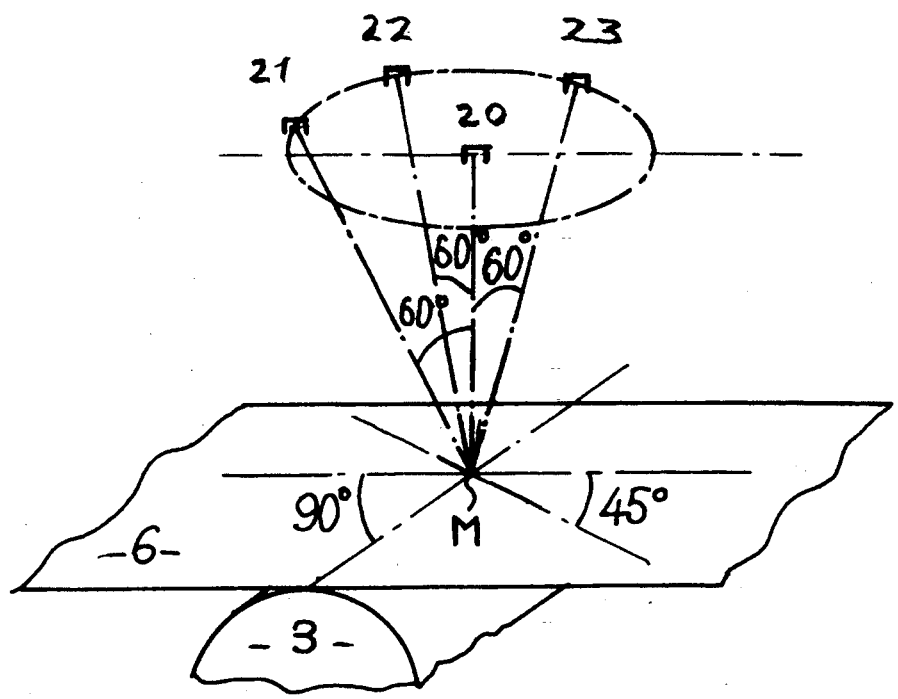
FIG. 5 is a diagrammatic view of an arrangement of goniometers above the sheet.

To measure the stresses in three directions above the point of contact of the sheet 6 with the roll 3 provided with a projecting torus-shaped boss, four goniometers 20, 21, 22, 23 aimed at the point M are employed (FIG. 5). The goniometer 20 is vertically above the point M. The goniometers 21, 22, 23 are inclined at 60° to the vertical and disposed in a circle so that:

the goniometer 21 is oriented in a direction of travel of the sheet;

the goniometer 23 is oriented in a direction perpendicular to the direction of travel of the sheet;

the goniometer 22 is oriented at 45° to the direction of travel of the sheet.

This device operates in a continuous manner. When it is placed at the output end of a sheet production line, it permits continuously regulating the parameters which have an effect on the mechanical properties of the sheet.

When the production line comprises a plurality of stages, a device may be provided at the output end of each stage and thereby regulate each component of the production line.

What is claimed is:

1. A method for continuously measuring mechanical properties of a sheet of steel, comprising:

producing on said sheet a known localized deformation which is such that at least in a zone of a surface of said sheet said deformation is partially plastic; and measuring in said zone of said surface at least one surface stress in a given direction, and wherein the step of measuring at least one surface stress is performed at least substantially simultaneous with the step of producing a known localized deformation.

2. Method according to claim 1, comprising for producing said partially plastic deformation of said sheet, rolling said sheet round a roll having a radius at least as small as a maximum radius size which will produce plastic deformation in said sheet when said sheet is passed therearound, to produce said partially plastic deformation by elongation of outer fibers of said sheet.

3. Method according to claim 2, comprising rolling said sheet round said roll which includes on a lateral surface of said roll a projecting torus-shaped boss.

4. Method according to claim 1, comprising evaluating said stresses by diffraction of X-rays.

5. A method for continuously measuring mechanical properties of a sheet of steel, comprising:

producing on said sheet a known localized deformation which is such that at least in a zone of a surface of said sheet said deformation is partially plastic; and measuring in said zone of said surface three surface stresses which are oriented:

a first surface stress in a direction of travel of said sheet;

a second surface stress in a direction perpendicular to said direction of travel of said sheet; and a third surface stress in an intermediate direction.

6. A method for continuously measuring mechanical properties of a sheet of steel, comprising:

producing on said sheet a known localized deformation by rolling said sheet round a roll having a radius which is small enough to produce a partially plastic deformation by elongation of outer fibers of said sheet, at least in a zone of a surface of said sheet, measuring in said zone of said surface at least one surface stress in a given direction, and wherein the step of measuring at least one surface stress is performed at least substantially simultaneous with the step of producing a known localized deformation, said roll having a lateral surface including a projecting torus-shaped boss.

7. A method for continuously measuring mechanical properties of a sheet of steel, comprising:

producing on said sheet a known localized deformation which is such that at least in a zone of a surface of said sheet said deformation is partially plastic;

measuring in said zone of said surface three surface stresses which are oriented:

one surface stress in a direction of travel of said sheet;

a second surface stress in a direction perpendicular to said direction of said travel of said sheet;

a third surface stress in an intermediate direction, wherein said producing and measuring steps include utilizing a roll having a lateral surface which includes a projecting torus-shaped boss, and four goniometers employing X-rays disposed in a region of said roll.

* * * * *